US008642954B2

(12) United States Patent
Ivaldi et al.

(10) Patent No.: US 8,642,954 B2
(45) Date of Patent: Feb. 4, 2014

(54) SAMPLE INTRODUCTION METHOD AND SYSTEM FOR ATOMIC SPECTROMETRY

(75) Inventors: Juan C. Ivaldi, Redding, CT (US); Cindy Anderau, Sandy Hook, CT (US); Peter J. Morrisroe, New Milford, CT (US); Kaveh Kahen, Maple (CA); Hamid Badiei, Woodbridge (CA)

(73) Assignee: PerkinElmer Health Sciences, Inc., Waltham, MA (US)

( * ) Notice: Subject to any disclaimer, the term of this patent is extended or adjusted under 35 U.S.C. 154(b) by 0 days.

(21) Appl. No.: 13/450,762

(22) Filed: Apr. 19, 2012

(65) Prior Publication Data

US 2012/0325925 A1 Dec. 27, 2012

Related U.S. Application Data

(60) Provisional application No. 61/477,453, filed on Apr. 20, 2011.

(51) Int. Cl.
*H01J 49/26* (2006.01)

(52) U.S. Cl.
USPC ............................ 250/288; 250/281; 250/282

(58) Field of Classification Search
USPC ......................................... 250/281, 282, 288
See application file for complete search history.

(56) References Cited

U.S. PATENT DOCUMENTS

| | | | | |
|---|---|---|---|---|
| 4,301,114 | A * | 11/1981 | Rounbehler et al. | 422/52 |
| 5,518,179 | A | 5/1996 | Humberstone et al. | |
| 5,838,350 | A | 11/1998 | Newcombe et al. | |
| 6,113,001 | A | 9/2000 | Sant et al. | |
| 7,316,067 | B2 | 1/2008 | Blakey | |
| 2009/0272894 | A1 * | 11/2009 | Shiokawa et al. | 250/282 |
| 2010/0006502 | A1 | 1/2010 | Schliefer | |

FOREIGN PATENT DOCUMENTS

JP 60079656 A 5/1985

* cited by examiner

*Primary Examiner* — Nicole Ippolito
(74) *Attorney, Agent, or Firm* — Cesari and McKenna, LLP

(57) ABSTRACT

A method of introducing a sample into an atomic spectrometer utilizes a spray head including a vibratable mesh. A liquid sample is conducted to one face of the mesh and the mesh is vibrated to expel sample droplets from the other face of the mesh into the proximal end of a flow passage axially spaced from the mesh. Also, a low pressure gas as flowed into the proximal end of the flow passage to mix with the droplets to form an aerosol in the flow passage. The vibrating of the mesh is controlled to provide in the aerosol a selected total volume of monodisperse droplets while the flow of the carrier gas is independently controlled to provide a selected rate of flow of the aerosol along the flow passage thereby to optimize consumption of the sample. Apparatus for practicing the method is also disclosed.

12 Claims, 5 Drawing Sheets

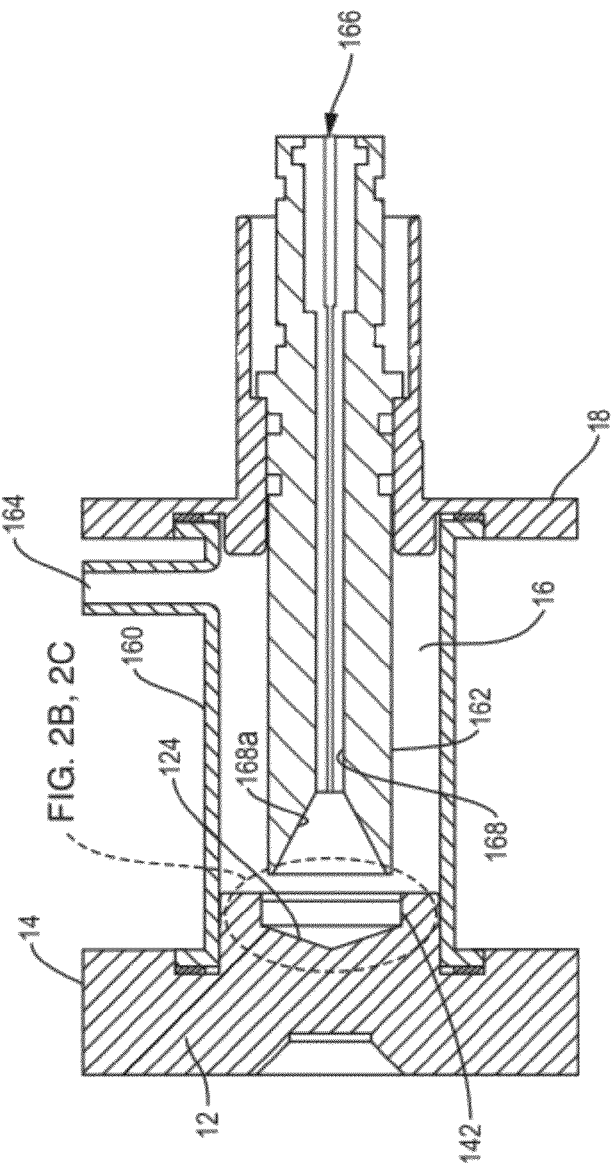
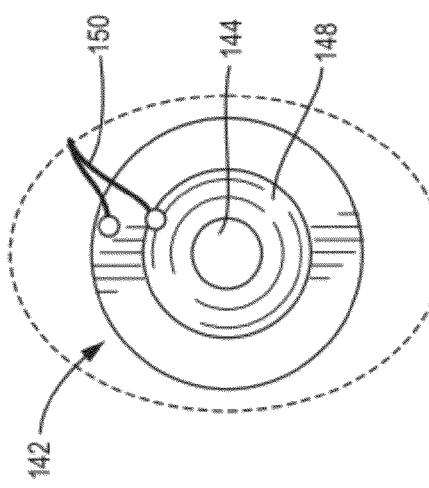
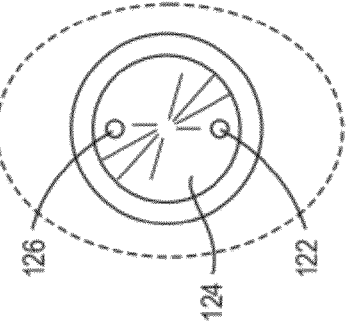

SAMPLE INTRODUCTION METHOD AND SYSTEM FOR ATOMIC SPECTROMETRY

CROSS-REFERENCE TO RELATED APPLICATION

This application claims the benefit of Provisional Patent Application Ser. No. 61/477,453, filed Apr. 20, 2011, the contents of which are incorporated by reference herein.

FIELD OF THE INVENTION

The technology described herein generally relates to systems, methods and devices for providing sample introduction for atomic spectrometry, and more particularly for use of a piezoelectric aerosol generator in a sample introduction system for atomic spectrometry.

BACKGROUND INFORMATION

Atomic spectrometry is an analytical technique useful for determining the elemental composition of a sample by its electromagnetic or mass spectrum. Typically atomic spectrometry methods are distinguished by the type of spectrometry used or the atomization source. Types of atomic spectrometry include optical and mass spectrometry. Optical spectrometry can be further divided into absorption, emission and fluorescence spectrometry. Systems for atomic spectrometry include any of a variety of atomization sources. Of atomization sources, flames are the most common due to their low cost and their simplicity. Inductively-coupled plasmas (ICP) are recognized for their outstanding analytical performance and their versatility. To perform atomic spectrometry analysis, the sample is vaporized and atomized. For atomic mass spectrometry, a sample must also be ionized. Vaporization, atomization, and ionization are often, but not always, accomplished with a single source. For efficiency in this process a sample to be analyzed is introduced into the source in droplet form. Pneumatic nebulizers are currently the most widely used sample introduction systems for ICP mass spectrometry.

Pneumatic nebulizers produce droplets of varying sizes and require spray sample chambers to essentially prevent larger droplets from being transported to the atomizer. Thus, a transport efficiency of 20% is expected, with roughly 80% of the sample being wasted. In addition, a peristaltic pump is typically required to deliver liquid to the nebulizer, and use of the pump results in the analytical precision of the measurement being tied to the liquid delivery rate of the pump. Further, the use of the pump tends also to introduce signal perturbations caused by the peristaltic pump pulsations.

SUMMARY OF THE INVENTION

Our improved sample introduction technique for use in atomic spectrometry systems utilizes a piezoelectric aerosol generator to produce a liquid aerosol with droplets in a narrow desired size range and a mixing or collection chamber in which the droplets are blended with a carrier gas that is at a relatively low pressure and has a desired flow rate. A control sub-system allows a user to actively control the volume of the aerosol introduced to the collection chamber and also independently control the flow rate of the carrier gas, to provide for optimized consumption of the sample.

The sample introduction system and method provides relatively high sample transport efficiency, on the order of 80% or more, utilizing relatively uniform distributions of droplets sized 10 microns or less. This is in contrast to the conventional sample introduction systems that employ pneumatic nebulizers, and which lose a high percentage of the sample to the elimination of overly large droplets in a spray sample chamber and/or to a lack of volume control. Further, the improved sample introduction system does not use a peristaltic pump, and may instead use pumps with lower pump rates, resulting in increased measurement precision.

Our improved sample introduction technique, which allows for independent adjustment of aerosol generation characteristics and ICP properties, provides improved analytical precision and improved speed, while also reducing sample waste.

BRIEF DESCRIPTION OF THE DRAWINGS

The technology is further described in the detailed description that follows, by reference to the noted drawings by way of non-limiting illustrative embodiments, in which like reference numerals represent similar parts throughout the drawings. As should be understood, however, the technology is not limited to the precise arrangements and instrumentalities depicted in the drawings, in which:

FIG. 1 is a schematic view of a sample introduction system constructed in accordance with an example embodiment for use with an atomic spectrometry system;

FIGS. 2A to 2C are more detailed schematic views of the sample introduction system of FIG. 1;

FIG. 3 is a schematic view of a control sub-system for the sample introduction system of FIG. 1;

FIG. 4 is a schematic view of electronic drive waveforms relating to an example embodiment;

FIG. 5 is a more detailed drawing of a perforated mesh utilized in the system of FIG. 1, and FIG. 6 is a fragmentary schematic view of another example embodiment of the sample introduction system.

DETAILED DESCRIPTION OF AN ILLUSTRATIVE EMBODIMENTS

In the following description, for purposes of explanation and not limitation, specific details are set forth, such as particular valves, adsorbents, sensors, heating devices, gases, materials, analytes, configurations, devices, ranges, temperatures, components, techniques, vessels, samples, and processes, etc. in order to provide a thorough understanding of the present invention.

However, it will be apparent to one skilled in the art that the present invention may be practiced in other embodiments that depart from these specific details. Detailed descriptions of well-known valves, adsorbents, sensors, heating devices, gases, materials, analytes, configurations, devices, ranges, temperatures, components, techniques, vessels, samples, and processes are omitted so as not to obscure the description of the present invention. As used in the description, the terms "top," "bottom," "above," "below," "over," "under," "above," "beneath," "on top," "underneath," "up," "down," "upper," "lower," "front," "rear," "back," "forward" and "backward" refer to the objects referenced when in the orientation illustrated in the drawings, which orientation is not necessary for achieving the objects of the invention.

The technology described herein relates to a sample introduction system for atomic spectrometry that utilizes piezoelectric aerosol generation. For ease of understanding, other component parts of atomic spectrometry system that operate in conventional manners are depicted in the drawings as a functional block 100 labeled "Atomic Spectrometer." The Atomic Spectrometer may be an IPC mass spectrometry system, an IPC optic emission system, and so forth.

Figure 1:
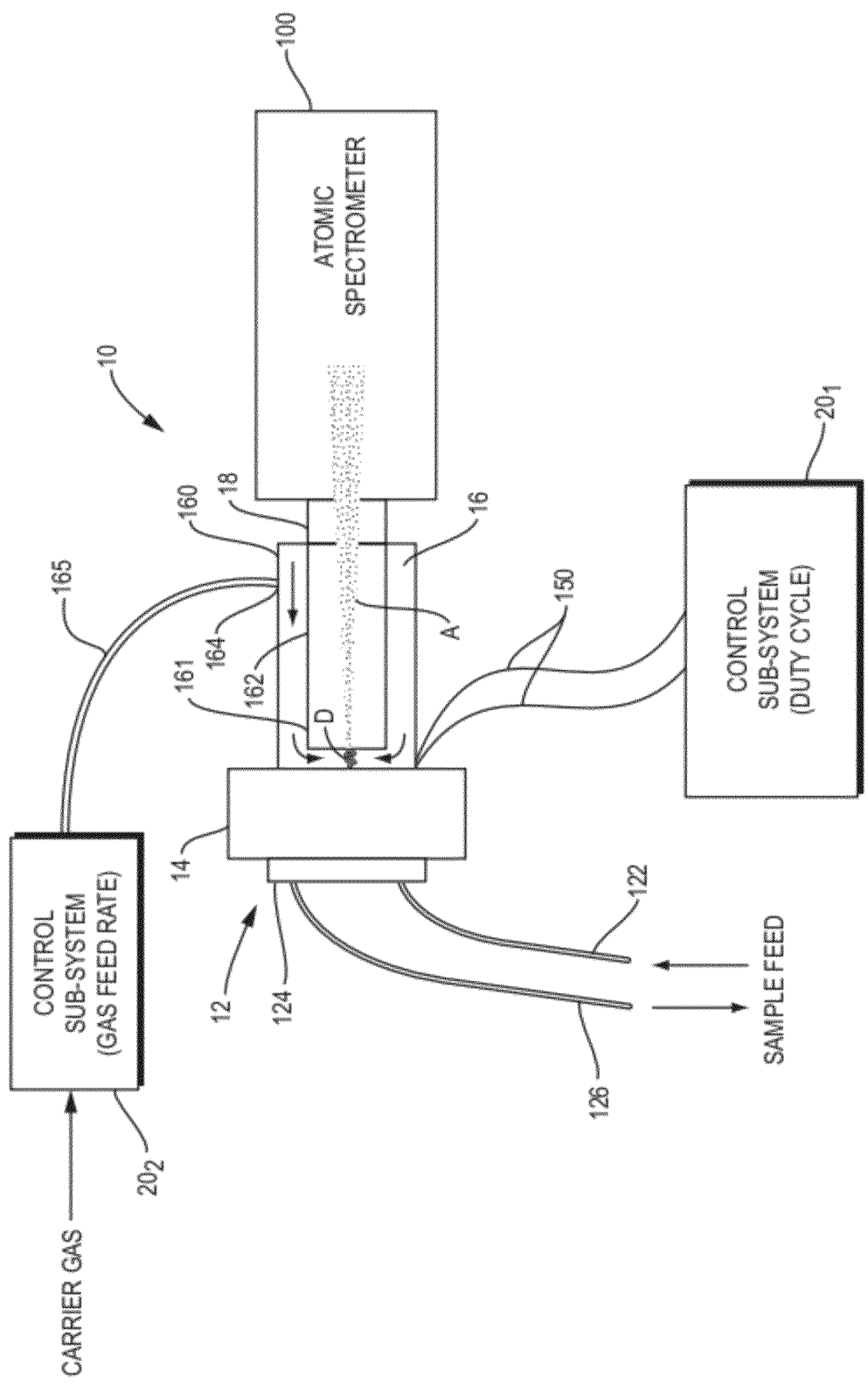

Referring to FIG. 1, the sample introduction system 10 employs a piezoelectric aerosol generator (PAG) that consists of a fluid feed sub-system 12, a spray head assembly 14, and a mixing chamber 16, in this example an argon collection system. The sample introduction system further includes a programmable controller having a user input keypad and which is depicted in FIG. 1 as component parts $20_1$ and $20_2$, that allows independent user control of droplet generation and carrier gas feed as will be described.

The PAG utilizes, in the spray head assembly 14, a spray head 142 (FIGS. 2A and 2B) that may be similar to spray heads described in U.S. Pat. Nos. 7,316,067; 5,518,179; 5,838,350 and 6,113,001, incorporated by reference herein in their entireties. However, in the sample introduction system 10, the material utilized for a perforated mesh component 144 of the spray head 14 is selected based, at least in part, on the properties of the sample. In one example, the sample is an acid and the mesh is made of steel or of a plastic, such as Kapton® polyimide film. Also, the diameters and configuration of nozzles 146, formed as perforations in the mesh 144, are selected to produce a desired burst quantity and size range of droplets. Micrographs of a suitable steel mesh 144 containing nozzles 146 in the form of tiny perforations is discussed below in connection with FIG. 5.

Referring now to FIGS. 1 and 2A-C, sample fluid from a fluid source (not shown) is provided to a fluid feed cavity 124 through a fluid feed inlet 122 and excess fluid is removed from the cavity through a fluid outlet 126. The fluid feed cavity 124 is sealed against the rear of the spray head 142 and presents to the spray head 142 the sample that is to be formed into droplets. The spray head 142 includes the mesh 144 in a laminated assembly that also includes a piezoelectric transducer and a substrate, which are together depicted in FIG. 2B by reference numeral 148. The control sub-system component $20_1$ connects to the transducer over lines 150 and provides a periodic drive waveform 400 (FIG. 4), such as a square wave or sine wave, to actuate the transducer, which, in turn, results in the vibration of the mesh 144. The operation of the control sub-system component $20_1$ is discussed below with reference to FIG. 4.

The mesh 144 acts as a gas-liquid interface. The liquid side is composed of the fluid feed system 12 that is configured to bring the sample into contact with the mesh. The gas side is the collection chamber 16 which receives sample droplets D issuing from the mesh.

As shown in FIGS. 1 and 2A, the collection chamber 16 consists of an outer tube 160 and an inner tube 162 defining the chamber 16 between them. A gas feed line 165 from subsystem $20_2$ provides a carrier gas e.g. argon, to the chamber through a gas inlet 164. Preferably, the gas should be under relatively low pressure, i.e. under 100 psi. The outer tube 160 thus provides a path for the low pressure carrier gas to flow to the gas interface of the mesh 144, or right to left in the directions of the arrows in FIG. 1. The outer tube directs the flow around a corner at the proximal end 161 of the inner tube 162 and the gas blends with the sample droplets D produced by the vibrating mesh 144 in spray head 142. The blended carrier gas and droplets then flow left to right as an aerosol A inside the inner tube 162 toward a source interface 18 leading into the atomizer (not shown) of the atomic spectrometer 100. In the embodiment depicted in FIG. 2A, a torch adapter 166 is integrated into the interior of the inner tube 162, to more precisely direct the aerosol A toward and into the source interface 18 at the distal end of the adapter 166. As best seen in that figure, the torch adaptor defines an axial passage 168 which may have a flared or funnel-shaped proximal end 168a that captures the droplets D and carrier gas and guides the blended aerosol A through the elongated body of the torch adapter 166. The shaped proximal end 168a of the passage essentially compensates for slight mis-alignments between the mesh 144 and the adaptor 166. The adaptor passage may instead have a proximal end 168a that is essentially the same diameter as passage 168, or one with slightly greater or lesser flare than the funnel-shaped end depicted in FIG. 2A.

Figure 3:
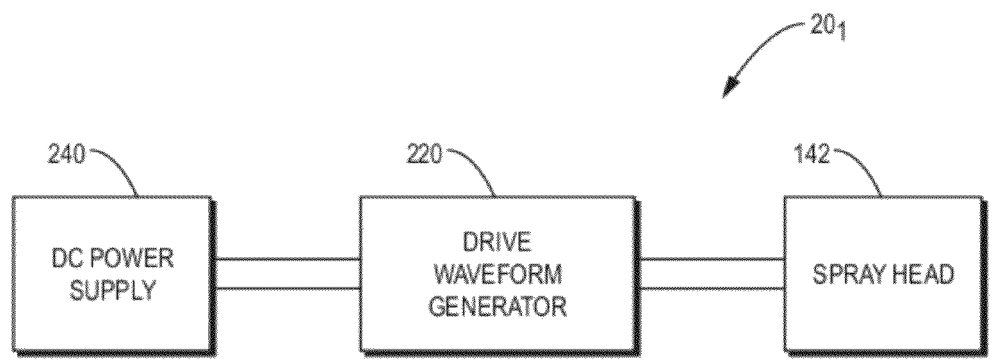
Figure 4:
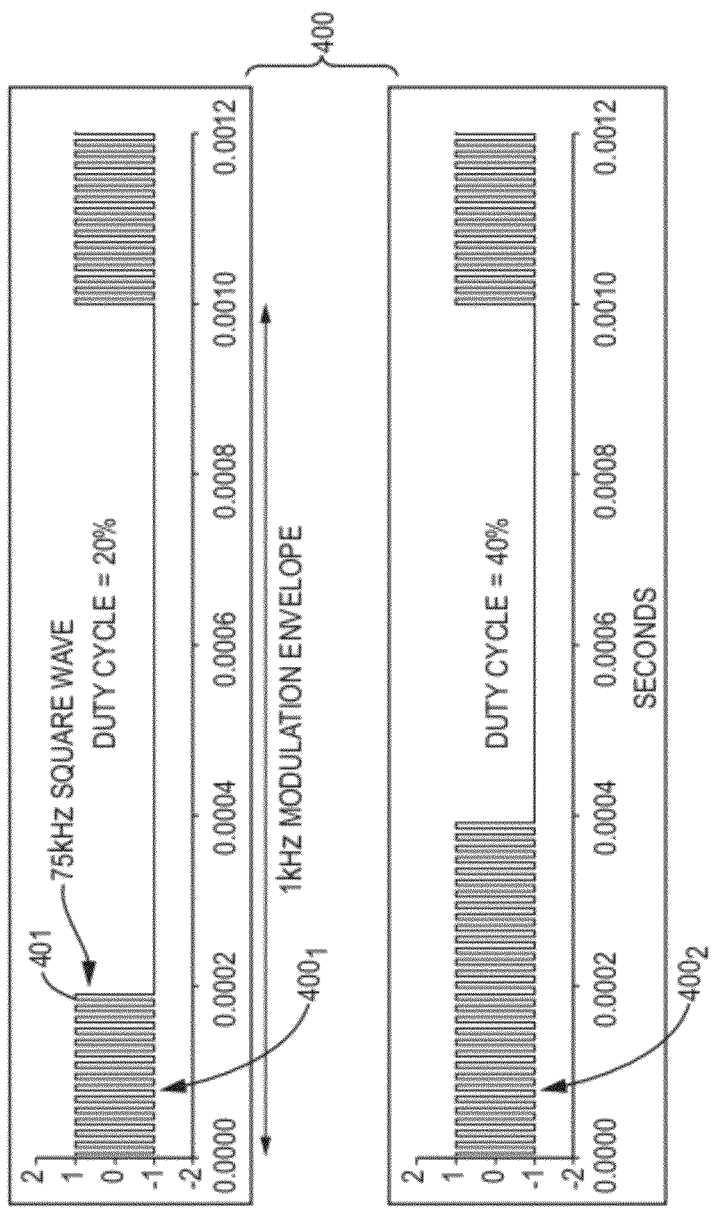

FIG. 3 depicts the control sub-system component $20_1$ in more detail. A drive waveform generator 220 operates in a known manner to produce a periodic drive waveform 400 (FIG. 4). The waveform duty cycle may be controlled by a user, by means of, for example, software control of generator 220. A DC power supply 240 provides power and relatively high voltage to the drive waveform generator 220, the two constituting a driver for the transducer. Example drive waveforms are depicted in FIG. 4. As shown there, the drive waveform $400_1$ is a square wave, illustrated as having a frequency of 75 kHz. The frequency of the drive waveform is selected to correspond to the resonant frequency of the spray head transducer 148 (FIG. 2B). The drive waveform $400_1$ has a duty cycle of 20% and thus drives the transducer, and, in turn, the vibration of the mesh 144 for 20% of a 1 kHz modulation envelope. The drive waveform $400_2$ has a duty cycle of 40% of the 1 kHz modulation envelope. The duty cycle is selected to control the total volume of the sample droplets that comprise the liquid aerosol A.

Figure 5:
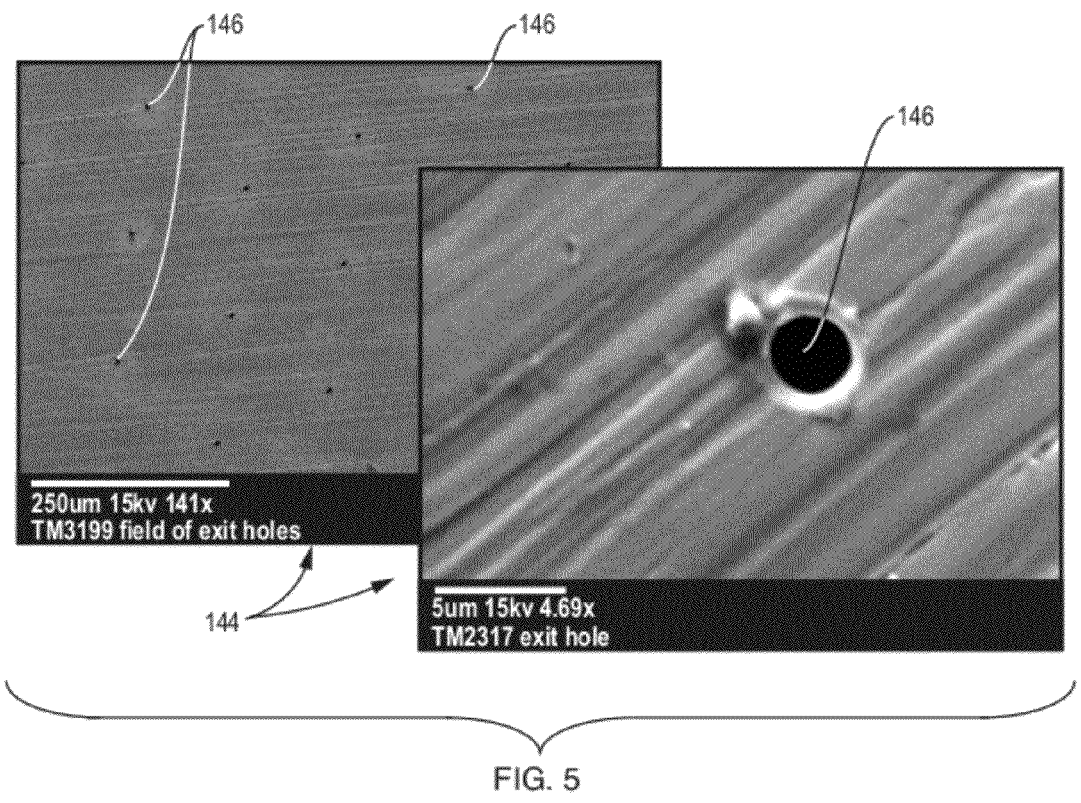

Referring to FIGS. 2B and 4, a transition 401 in the square wave 400 activates the transducer, which, in turn, causes the mesh 144 to vibrate, and droplets D of the sample are produced by the respective nozzles 146. When, for example, the mesh vibrates in the direction of the cavity 124, the nozzles pick up liquid from the cavity, and when the mesh then vibrates in the opposite direction, the nozzles eject the liquid out of the opposite side as droplets D. Accordingly, a known quantity of droplets in a uniform droplet distribution is produced in response to each signal transition in the drive waveform. The mesh 144, shown in enlarged formats in FIG. 5, is a thin steel sheet with laser-drilled holes of a selected diameter that form the nozzles 146. An example of the nozzle size is 2 microns, which produces droplets in a narrow range of sizes smaller than 10 microns. The nozzles in the desired configuration are separated by a selected distance, for example, 70 microns. The selected size, number and separation of the nozzles in the mesh 144 results in a desired burst quantity of monodisperse droplets D. By controlling the duty cycle of the drive waveform, a user can precisely control the volume of the sample by controlling the rate of drop bursting in the aerosol A. This is in contrast to the conventional pneumatic nebulizer, which does not allow for such user volume control.

Figure 6:
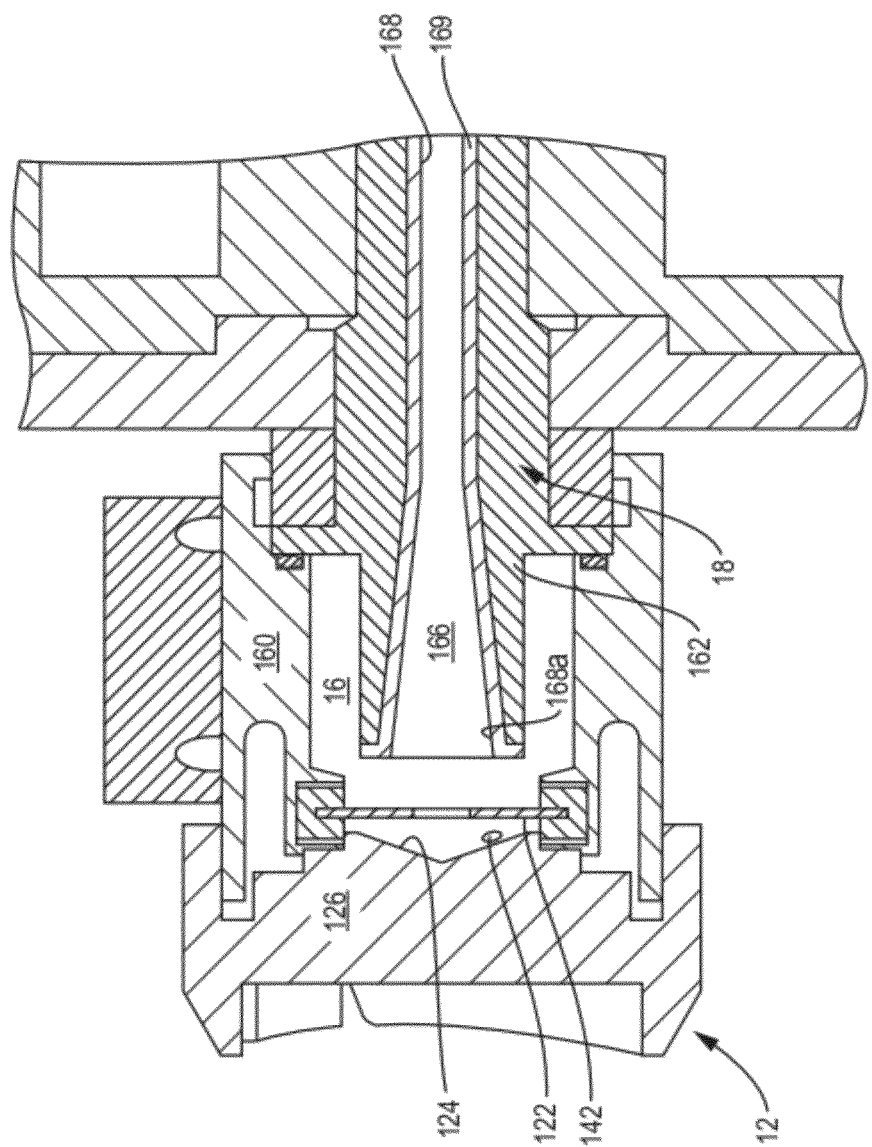

Referring now to FIG. 6, another embodiment of the sample introduction system 10 utilizing PAG is shown for an atomic spectrometer 100 (FIG. 1). As before, the fluid feed system 12 includes a fluid feed cavity 124 and a fluid feed inlet 122 that leads to the fluid cavity 124 which, in turn, holds a liquid against the liquid interface of the spray head 142. The fluid outlet 126 from the fluid cavity is not visible in the orientation of this drawing. A carrier gas, such as argon, is introduced to the outer tube 160 through a gas inlet, which is also not visible in the orientation of this drawing. The carrier gas flows along chamber 16 into contact with droplets produced by the spray head 142, and a blend of the droplets and the carrier gas is directed as an aerosol along the axial passage 168 of the torch adaptor 166 into and through the source interface 18 to the remainder of the system shown in FIG. 1.

The proximal end 168a of the adapter passage 168 is much more gradually flared than the flared end of the adapter 166 in FIG. 2A. Also, tube 162 is joined to the elongated body 169 of the adapter to simplify construction and allow for better alignment of the liquid and gas sides of the apparatus.

As discussed above, the control sub-system component $20_2$ of the sample introduction system 10 provides user control of the carrier gas flow rate independently of the aerosol generation controlled by sub-system $20_1$. Unlike the pneumatic nebulizer, the present sample introduction system does not require a high pressure gas stream. Accordingly, a user, through sub-system $20_2$, can readily control the gas flow rate of the relatively low pressure carrier gas by controlling an associated valve or pump (not shown), manually or through software control.

Independently controlling aerosol generation and carrier gas flow rate produces a higher quality aerosol and greater transport efficiency, which results in increases in detection limits. Furthermore, the precise control of aerosol generation provides the ability to produce multi-point calibration curves from fewer or even a single standard. In addition, the precise control results in less sample production and optimized consumption such that sample waste is reduced overall. In addition, the control may lead to a reduction in the amount of sample being transported into an injector (not separately shown) of the atomic spectrometer 100 at times when the optical sensing of signal is not occurring but when a matrix-laden solution is present at the liquid interface of the mesh 144. This may, in turn, result in reduced need for, or frequency of, system maintenance.

High transport efficiency (>80%), uniform droplet size and consistent flow rate were observed when the improved sample introduction system, employing the PAG and providing sample volume control and/or independent gas flow rate control, was utilized for ICP optical emission spectrometry (OES). These attributes result in demonstrated improvements in the analytical figures of merit for ICP OES. By comparison, known sample nebulizers used in ICP OES produce aerosols either pneumatically or with an ultrasonic transducer, both of which are less efficient and less precise because they produce poly-disperse aerosols which require use of a spray chamber to remove the largest fraction of droplets, thereby generating a large proportion of waste. A significant fraction of droplets are further lost in transport, with transport efficiencies of 1-5 percent being common for pneumatic nebulizer/spray chamber arrangements.

It is to be understood that the foregoing illustrative embodiments have been provided merely for the purpose of explanation and are in no way to be construed as limiting of the invention. Words used herein are words of description and illustration, rather than words of limitation. In addition, the advantages and objectives described herein may not be realized by each and every embodiment practicing the present invention. Further, although the invention has been described herein with reference to particular structures, materials and/or embodiments, the invention is not intended to be limited to the particulars disclosed herein. Rather, the invention extends to all functionally equivalent structures, methods and uses, such as are within the scope of the appended claims. Those skilled in the art, having the benefit of the teachings of this specification, may affect numerous modifications thereto and changes may be made without departing from the scope and spirit of the invention.

What is claimed is:

1. A sample introduction system for atomic spectrometry comprising:
    a spray head including a mesh having opposite faces, a sample flow path for conducting a liquid sample to one face of the mesh and a transducer for vibrating the mesh;
    a driver for driving the transducer to expel sample droplets from the other face of the mesh;
    an elongated tubular adapter defining a flow passage having a proximal end aligned with and spaced from the mesh and a distal end;
    a tubular wall surrounding a proximal end segment of the elongated tubular adapter to define a chamber in fluid communication with said other face of the mesh and with said proximal end of the flow passage;
    a carrier gas source connected to the chamber;
    a flow control device for controlling the flow of gas from the carrier gas source to the chamber so that the gas can mix with any sample droplets expelled from the mesh to form an aerosol in the flow passage, and
    a controller for controlling the driver to provide in said aerosol a selected total volume of monodisperse droplets and for independently controlling said flow control device to provide a selected rate of flow of the aerosol along said flow passage thereby to optimize consumption of the liquid sample.

2. The system defined in claim 1 wherein the proximal end of said flow passage has a funnel shape.

3. The system defined in claim 2 wherein the funnel shape extends axially beyond the chamber.

4. The system defined in claim 1 wherein the carrier gas is argon.

5. The system defined in claim 1 wherein the driver comprises:

a DC power supply, and a waveform generator connected between the DC power supply and the transducer, said controller controlling the waveform generator to deliver to the transducer a periodic voltage waveform having a frequency corresponding to a resonant frequency of the transducer.

6. The system defined in claim 5 wherein the controller controls a duty cycle of the voltage waveform.

7. The system defined in claim 5 wherein the periodic voltage waveform is a sine wave or a square wave.

8. The system defined in claim 1 wherein the mesh comprises a thin sheet containing a multiplicity of perforations having a selected size and a selected separation.

9. The system defined in claim 8 wherein the thin sheet is of an acid-resistant metal or plastic material.

10. The system defined in claim 1 wherein said sample flow path includes:

a housing defining a cavity facing said one face of the mesh;

an inlet into the cavity, said inlet being connected to a sample source; and an outlet from the cavity, said inlet and outlet being spaced apart so that the liquid sample is directed across said one face of the mesh.

11. A method of introducing a sample into an atomic spectrometer, said method comprising the steps of:

providing a spray head including a vibratable mesh;

conducting a liquid sample to one face of the vibratable mesh;

vibrating the vibratable mesh to expel sample droplets from the other face of the mesh into a proximal end of a flow passage axially spaced from the vibratable mesh;

conducting a low pressure gas into the proximal end of the flow passage to mix with the sample droplets to form an aerosol in the flow passage;

controlling the vibrating to provide in the aerosol a selected total volume of monodisperse droplets; and independently controlling the flow of the low pressure gas to provide a selected rate of flow of said aerosol along the flow passage thereby to optimize consumption of the liquid sample.

12. The method defined in claim 11 wherein the vibrating step is carried out by a transducer contacting the vibratable mesh, and the vibrating control step is accomplished controlling a duty cycle of a voltage waveform applied to the transducer.

* * * * *